United States Patent [19]

White

[11] Patent Number: 4,704,484
[45] Date of Patent: Nov. 3, 1987

[54] PREPARATION OF FLUORINATED ORGANIC COMPOUNDS

[75] Inventor: David H. White, Florissant, Mo.

[73] Assignee: Mallinckrodt, Inc., St. Louis, Mo.

[21] Appl. No.: 543,433

[22] Filed: Oct. 19, 1983

[51] Int. Cl.$^4$ ............................................. C07C 25/24
[52] U.S. Cl. .................................... 570/128; 570/142; 570/143
[58] Field of Search ............... 570/128, 142, 147, 144, 570/164, 173, 143; 424/1.1; 260/694; 564/412, 442

[56] References Cited

U.S. PATENT DOCUMENTS

| | | | |
|---|---|---|---|
| 2,549,565 | 4/1951 | Benner | 570/123 |
| 2,702,306 | 2/1955 | Gall et al. | 260/650 |
| 3,221,069 | 11/1965 | Bain et al. | 564/412 |
| 3,399,179 | 8/1968 | Grakauskus | 570/142 |
| 3,833,581 | 9/1974 | MacKenzie et al. | 570/147 |
| 4,205,085 | 5/1980 | Shepherd | 570/142 |
| 4,222,968 | 9/1980 | Schack et al. | 570/173 |

OTHER PUBLICATIONS

Wilson, C. V., *Organic Reactions*, 9, 332, (1957).
Kochi, J. K., *J. Am. Chem. Soc.*, 87, 2500, (1965).

*Primary Examiner*—Natalie Trousof
*Assistant Examiner*—Joseph A. Boska
*Attorney, Agent, or Firm*—Bernard, Rothwell & Brown

[57] ABSTRACT

This invention relates to the fluorination of carboxylic acids with xenon difluoride in the presence of hydrogen fluoride. Novel fluorinated compounds containing aliphatic unsaturation are also disclosed.

2 Claims, No Drawings

PREPARATION OF FLUORINATED ORGANIC COMPOUNDS

BACKGROUND OF INVENTION

This application is directed to the fluorination of organic compounds. More specifically, there is disclosed a process for the fluoro-decarboxylation of carboxylic acid compounds.

Attempts to effect the fluorination of organic compounds employing elemental fluorine as the fluorinating agent have resulted in a high degree of fluorolysis and consequently in low yields of desired fluorinated products. Such processes employing solid catalyst masses have proved to be exceedingly cumbersome and difficult to control. One method for fluorinating an organic compound is disclosed in U.S. Pat. No. 2,549,565. This process comprises separately and simultaneously injecting the organic compound and elemental fluorine (gas) into a molten mass consisting of from 20 percent to 70 percent of silver monofluoride and from 80 percent to 30 percent of silver difluoride mainained at a temperature between 200° C. and 500° C.

U.S. Pat. No. 2,702,306 discloses another method of producing organic fluorine compounds. This method consists of reacting halogen fluorides with fluorinatable organic materials, wherein the halogen fluoride is mixed with hydrogen fluoride in concentrations of 10 to 90 percent by weight halogen fluoride and contacting this mixture in the liquid phase with the fluorinatable organic material.

U.S. Pat. No. 3,221,069 discloses a method in which a halogen atom can be introduced into an aromatic compound. This process comprises heating an aromatic carboxylic acid halide at a temperature of from about 200° C. to about 400° C. in the presence of a palladium catalyst.

The production of fluorine-substituted aromatic compounds has been accomplished by utilizing $XeF_2$ in liquid $CCl_4$ solution and carrying out the substitution at extremely low temperatures, such as $-70°$ C. After the substitution reaction is complete, the solvent is then removed. Unfortunately, the substitution reaction is quite slow and the reaction equipment is expensive.

Yet another process of producing a fluorine-substituted aromatic compound is disclosed in U.S. Pat. No. 3,833,581. This process comprises the step of reacting certain aromatic compounds in the vapor phase with xenon difluoride vapor at a temperature of about 200° C. and a mole ratio of xenon difluoride to said aromatic compound of no greater than one. Unfortunately, this process requires expensive reaction vessels that can cool the reactants to $-78°$ C.

Halogenated organic compounds have previously been prepared by halo-decarboxylation reactions. In the "Hunsdiecker reaction" the silver salt of a carboxylic acid is reacted with a halogen, which displaces the carboxyl group (see Wilson, C. V., *Organic Reactions*, 9, 332 [1957]). In another halo-decarboxylation reaction, an ionic halide salt is reacted with a carboxylic acid in the presence of lead tetraacetate (Kochi, J. K., *J. Am. Chem. Soc.*, 87, 2500 [1965]). But these halo-decarboxylation reactions are limited to halogens other than fluorine.

SUMMARY OF THE INVENTION

The present invention provides a process for fluorinating an organic compound which comprises reacting a carboxylic acid with xenon difluoride in the presence of hydrogen fluoride, wherein said carboxylic acid is of the formula:

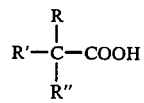

wherein R, R', and R'' are each, individually, a radical selected from the group consisting of hydrogen; halo; carboxyl; alkyl of 1 to 25 carbon atoms; alkoxy of 1 to 25 carbon atoms; aryl-substituted alkyl, alkenyl or alkynyl of 7 to 32 carbon atoms; aryl of from 6 to 14 carbon atoms; aryloxyalkyl of 6 to 32 carbon atoms; alkyl substituted aryl of 7 to 32 carbon atoms; alkenyl of 2 to 25 carbon atoms; and alkynyl of 2 to 25 carbon atoms, said radical being unsubstituted or substituted by one or more halo, carboxyl, acyl, acyloxy, nitro, amino or acylamino groups.

Surprisingly, when the R, R' or R'' radical contains aliphatic unsaturation, fluorination occurs only at the carboxyl site and the unsaturated bonds remain intact.

There are also provided, in accordance with the process of the invention, novel unsaturated compounds of the formula:

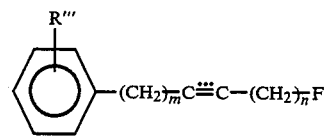

wherein m and n are integers of at least 1, such that the sum of m+n is from 2 to 24; the bond represented by the dotted line may be hydrogenated; and R''' is hydrogen, halo, acyl, acyloxy, nitro, amino or acylamino. The compounds are useful as pesticides.

The novel unsaturated compounds can be prepared, according to the process of this invention, by fluorinating a carboxylic acid of the formula:

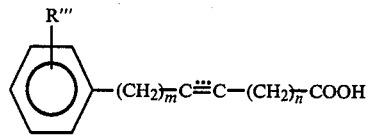

DESCRIPTION OF THE PREFERRED EMBODIMENT

The present invention involves the fluorination of carboxylic acids. More specifically it relates to the reaction of xenon difluoride with carboxylic acids in the presence of hydrogen fluoride, resulting in a selective substitution of the carboxyl group with fluorine. For example, phenylacetic acid is reacted with xenon difluoride in the presence of hydrogen fluoride to produce benzyl fluoride.

The carboxylic acid compounds which are fluorinated in the process of the present invention are of the structural formula:

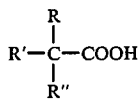

where R, R' and R" are as described above. A preferred aryl moiety in the groups R, R' and R" is phenyl. Examples of carboxylic acids which can be fluorinated by the process of the invention include acetic acid, propionic acid, palmitic acid, capric acid, phenylacetic acid, phenylpropionic acid, hydrocinnamic acid, 2-iodomalonic acid, octanoic acid, ethoxyacetic acid, 15-[4-(carboxymethylene)phenyl]pentadecanoic acid methyl ester, 4-phenylbut-3-enoic acid, 4-carboxyphenylacetic acid, 4-nitrophenoxyacetic acid, 1,18-octadec-8-endioc acid mono methyl ester, 1,18-octadec-8-yndioic acid monomethyl ester and iodoacetic acid.

The resultant fluorinated compounds in which at least one of R, R' and R" is carboxyl, halo, aryl or aryloxy are useful as pharmaceutical intermediates. Compounds in which at least one of R, R'. and R" is alkyl, alkenyl, alkynyl or aryl-substituted alkynyl are useful as pesticides. Compounds in which at least one of R, R' and R" is alkoxy are useful as industrial solvents. Compounds in which at least one of R, R' and R" is aryl-substituted alkyl or alkyl-substituted aryl are useful as NMR imaging agents. Compounds in which at least one of R, R' and R" is aryl-substituted alkenyl are useful as polymer additives.

If desired, one may carry out the fluorination according to the process of the invention using radioisotopic fluorinating agents, i.e. xenon difluoride and hydrogen fluoride in which the fluorine is $^{18}F$, to produce compounds useful as radiopharmaceuticals, e.g. heart imaging agents. Particularly useful for such applications are compounds in which at least one of R, R' and R" is alkenyl, alkynyl aryl-substituted alkyl or alkyl-substituted aryl.

In accordance with the preferred embodiment, the carboxylic acid is placed in a suitable reactor and the xenon difluoride is then added. Thereafter, the hydrogen fluoride is introduced to the reactants, for example, by bubbling through the reaction mixture. Preferably, the mixture is stirred to insure sufficient contact of the reactants. After the reaction is complete, water or a dilute base solution is charged to the reactor. The organic layer is then removed and the fluorinated product is isolated.

The reaction can be carried out in a conventional reaction vessel. Preferably, the reaction vessel is a closed vessel equipped with means for stirring the reaction mixture and for controlling the temperature of the reaction mixture as well as means for introducing the hydrogen fluoride into the reaction mixture, e.g. a sparging tube. Since hydrogen fluoride will react with glass, the reaction vessel is preferably not glass lined.

The xenon difluoride can be provided to the reaction mixture in an amount from about 0.7 to 1.3 moles per mole of carboxylic acid, preferably from about 0.9 to 1.1 moles per mole of carboxylic acid.

The amount of hydrogen fluoride introduced to the reaction is not narrowly critical as long as a sufficient amount of hydrogen fluoride is brought into intimate contact with reactants to catalyze the reaction. This can be achieved by slowly bubbling hydrogen fluoride through the reaction mixture at the start of the reaction.

The temperature of the reaction between the xenon difluoride, carboxylic acid and hydrogen fluoride is not narrowly critical. Typically, the reaction can be conducted at a temperature of from 0° C. to 60° C. Preferably, the reaction is conducted at room temperature.

The reaction time can vary depending on the starting materials, reaction conditions and volume of reactants. Typically, the reaction proceeds to completion in about 1 to 24 hours.

The pressure at which the reaction is carried out has not been found to be critical, however, the reaction can be conducted at atmospheric or superatmospheric pressures, preferably at atmospheric.

Advantageously the reaction can be carried out in the presence of a solvent. It will be apparent to those skilled in the art any conventional solvent is suitable as long as its presence does not interfere with the fluorination reaction. Chlorinated solvents are generally preferred. Some examples are methylene chloride, chloroform and carbon tetrachloride.

The following examples are supplied in order to illustrate, but not necessarily to limit, the process of the present invention.

EXAMPLE 1

Preparation of 12-Fluoro-1-(4-iodophenyl)-4-dodecyne). A solution of 6 ml of dichloromethane containing 0.2 grams (0.5 mM) of an acid of the following structural formula:

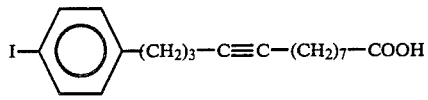

was placed in a plastic bottle which was connected to a drying tube and a hydrogen fluoride cylinder. After $XeF_2$ (0.21 g, 1.25 mM) was added, hydrogen fluoride was added. Several drops of liquid came out of the hydrogen fluoride container and went into the reaction bottle. The reaction mixture formed two layers. The mixture was stirred for five hours at room temperature and then the mixture was poured into ice water. The reaction mixture was then extracted with ethyl ether. The ether extract was washed with water and brine. The mixture was then dried over sodium sulfate, the solvent was removed to give 0.22 grams of crude product. The major product (0.07 grams) was isolated by high pressure liquid chromotography on a C-18 reverse phase column. Its ir spectrum and nmr spectra (H-1, C-13 and F-19) were consistent with the structure below:

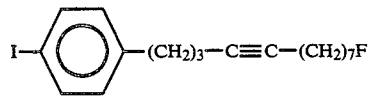

High resolution mass spectroscopy showed a molecular ion at 386.0910 M/e which was consistent with the calculated value of 386.09058 for $C_{18}H_{24}FI$. It was quite surprising that fluorination occurred selectively at the carboxyl site and that no fluorination occurred at the site of acetylenic unsaturation.

EXAMPLES 2–11

In a manner similar to that of Example 1, the carboxylic acids listed as starting materials in Table I are fluorinated in the presence of xenon difluoride and hydrogen fluoride. In Examples 5, 9 and 10, the xenon difluoride and hydrogen fluoride employed incorporate radioisotopic fluorine, i.e. $^{18}F$.

TABLE I

| Example | Starting Material and Formula | Product and Formula |
|---|---|---|
| 2 | 2-iodamalonic acid<br>$HOOC-CHI-COOH$ | difluoroiodomethane<br>$F-CHI-F$ (or $ICHF_2$) |
| 3 | octanoic acid<br>$CH_3(CH_2)_7COOH$ | fluorooctane<br>$CH_3(CH_2)_7F$ |
| 4 | ethoxyacetic acid<br>$CH_3CH_2O-CH_2-COOH$ | ethoxyfluoromethane<br>$CH_3CH_2O-CH_2F$ |
| 5 | 15-[4-carboxymethylene)phenyl]pentadecanoic acid methyl ester<br>$HOOC-CH_2-\text{C}_6\text{H}_4-(CH_2)_{14}-COOCH_3$ | $^{18}F$-labeled 15-[4-(fluoromethyl)phenyl]pentadecanoic acid<br>$^{18}FCH_2-\text{C}_6\text{H}_4-(CH_2)_{14}-COOH$ |
| 6 | 4-phenylbut-3-enoic acid<br>$CH=CHCH_2-COOH$ | 3-fluoro-1-phenyl-1-propene<br>$CH=CHCH_2F$ |
| 7 | 4-carboxyphenylacetic acid<br>$HOOC-\text{C}_6\text{H}_4-CH_2-COOH$ | 4-(fluoromethyl)-benzoic acid<br>$HOOC-\text{C}_6\text{H}_4-CH_2F$ |
| 8 | 4-nitrophenoxyacetic acid<br>$NO_2-\text{C}_6\text{H}_4-OCH_2-COOH$ | 4-(fluoromethyoxy)-nitrobenzene<br>$NO_2-\text{C}_6\text{H}_4-OCH_2F$ |
| 9 | 1,18-octadec-8-endioic acid monomethyl ester<br>$HOOC-(CH_2)_7-CH=CH-(CH_2)_7COOCH_3$ | $^{18}F$-labeled 17-fluoroheptadec-8-enoic acid<br>$^{18}F(CH_2)_7CH=CH-(CH_2)_7COOH$ |
| 10 | 1,18-octadec-8-yndioic acid monomethyl ester<br>$HOOC-(CH_2)_7-C\equiv C-(CH_2)_7COOCH_3$ | $^{18}F$-labeled 17-fluoroheptadec-8-ynoic acid<br>$^{18}F(CH_2)_7C\equiv C-(CH_2)_7COOH$ |
| 11 | iodoacetic acid<br>$ICH_2COOH$ | fluoroiodomethane<br>$ICH_2F$ |

I claim:

1. The compound of the formula:

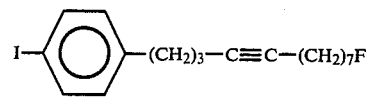

2. A process for fluorinating a carboxylic acid comprising reacting a carboxylic acid of the formula:

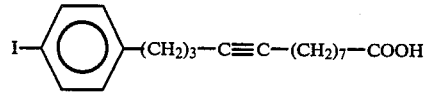

with xenon difluoride in the presence of hydrogen fluoride.